US008346369B2

(12) United States Patent
Mahajan et al.

(10) Patent No.: US 8,346,369 B2
(45) Date of Patent: Jan. 1, 2013

(54) SYSTEMS AND METHODS FOR PROGRAMMING IMPLANTABLE MEDICAL DEVICES

(75) Inventors: Deepa Mahajan, Circle Pines, MN (US); Yanting Dong, Shoreview, MN (US); Muhammad A. Ahmad, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 421 days.

(21) Appl. No.: 12/777,680

(22) Filed: May 11, 2010

(65) Prior Publication Data

US 2010/0318155 A1  Dec. 16, 2010

Related U.S. Application Data

(60) Provisional application No. 61/178,096, filed on May 14, 2009.

(51) Int. Cl.
*A61N 1/08* (2006.01)
(52) U.S. Cl. ............................................. 607/59; 607/30
(58) Field of Classification Search ...................... 607/59
See application file for complete search history.

(56) References Cited

U.S. PATENT DOCUMENTS

| | | | |
|---|---|---|---|
| 5,716,382 A * | 2/1998 | Snell | 607/30 |
| 5,893,883 A * | 4/1999 | Torgerson et al. | 607/59 |
| 6,336,903 B1 | 1/2002 | Bardy | |
| 6,669,631 B2 | 12/2003 | Norris et al. | |
| 7,009,511 B2 | 3/2006 | Mazar et al. | |
| 7,181,375 B2 | 2/2007 | Rao et al. | |
| 7,191,006 B2 * | 3/2007 | Hu et al. | 607/30 |
| 7,299,194 B1 | 11/2007 | Manganaris et al. | |

(Continued)

FOREIGN PATENT DOCUMENTS

WO    WO2010132592 A3    11/2010

OTHER PUBLICATIONS

Agrawal, Rakesh "Mining Association Rules between Sets of Items in Large Databases", *Proceedings of the 1993 ACM SIGMOD Conference* Washington DC, USA, May 1993, pp. 1-10.

(Continued)

*Primary Examiner* — Kennedy Schaetzle
(74) *Attorney, Agent, or Firm* — Pauly, Devries Smith & Deffner, L.L.C.

(57) ABSTRACT

Embodiments of the invention are directed to systems and methods for programming implantable medical devices, amongst other things. In an embodiment, the invention includes a method of programming an implantable medical device. The method can include gathering parameter data representing a set of previously programmed parameter values from a plurality of implanted medical devices. The method can further include performing association analysis on the parameter data to form a set of association rules. The method can further include suggesting parameter choices to a system user regarding a specific patient based on the set of association rules. In an embodiment, the invention can include a medical system including a server configured to perform association analysis on a set of data representing previously programmed parameter values from a plurality of implanted medical devices to derive a set of association rules. Other embodiments are also included herein.

20 Claims, 8 Drawing Sheets

U.S. PATENT DOCUMENTS

| | | |
|---|---|---|
| 7,461,006 B2 | 12/2008 | Gogolak |
| 8,032,229 B2 * | 10/2011 | Gerber et al. ............... 607/62 |
| 8,155,749 B2 * | 4/2012 | Lee et al. ............... 607/59 |
| 2003/0120514 A1 | 6/2003 | Rao et al. |
| 2004/0068199 A1 | 4/2004 | Echauz et al. |
| 2004/0117204 A1 | 6/2004 | Mazar |
| 2004/0119712 A1 | 6/2004 | Kenknight et al. |
| 2005/0065555 A1 | 3/2005 | Er |
| 2005/0080462 A1 * | 4/2005 | Jenkins et al. ............... 607/58 |
| 2006/0195039 A1 | 8/2006 | Drew |
| 2007/0179349 A1 | 8/2007 | Hoyme et al. |
| 2010/0132592 A1 | 6/2010 | Nagamizu et al. |

OTHER PUBLICATIONS

Exarchos, T. P. "An association rule mining-based methodology for automated detection of ischemic ECG beats", *IEEE Transactions on Biomedical Engineering* vol. 53, No. 8 Aug. 2006.

Tan, Pang-Ning et al., "Introduction to Data Mining", May 2, 2005, Chapter 6; pp. 328-414.

"PCT International Search Report and Written Opinion", *from International Application No. PCT/US2010/034587, corresponding to U.S. Appl. No. 12/777,680*, mailed Nov. 2010, (pp. 1-16).

* cited by examiner

SYSTEMS AND METHODS FOR PROGRAMMING IMPLANTABLE MEDICAL DEVICES

This application claims the benefit of U.S. Provisional Application No. 61/178,096, filed May 14, 2009, the contents of which are herein incorporated by reference.

TECHNICAL FIELD

This disclosure relates generally to implantable medical devices, and more particularly, to system and methods for programming implantable medical devices, amongst other things.

BACKGROUND OF THE INVENTION

Implantable medical devices (IMDs) are commonly used to provide treatment to patients. Implantable medical devices can include cardiac rhythm management devices and neurological stimulation devices, amongst others. Some types of implantable medical devices deliver electrical stimuli to a target tissue via a lead wire ("stimulation lead") or catheter having one or more electrodes disposed in or about the target tissue.

Modern IMDs of the type that include an onboard processor are generally highly programmable. Many different parameters can have nominal values that can be adjusted by a care provider, such as a doctor. For example, in the context of a pacing device, parameters can include pacing amplitude, pacing rate, pulse width, and the like.

Association analysis is an analytical technique that can be used to discover relationships within data sets. As one example, association analysis has been used to analyze market basket transactions in order to derive relationships between different items purchased by consumers at a store.

SUMMARY OF THE INVENTION

Embodiments of the invention are directed to systems and methods for programming implantable medical devices, amongst other things. In an embodiment, the invention includes a method of programming an implantable medical device. The method can include gathering parameter data representing a set of previously programmed parameter values from a plurality of implanted medical devices. The method can further include performing association analysis on the parameter data to form a set of association rules. The method can further include suggesting parameter choices to a system user regarding a specific patient based on the set of association rules.

In an embodiment, the invention includes a method of programming an implantable medical device including gathering parameter data representing a set of previously programmed parameter values from a plurality of implanted medical devices. The method can also include gathering outcome data representing the effects achieved by the previously programmed parameter values from the plurality of implanted medical devices. The method can also include linking the parameter data with the corresponding outcome data to form a master data set. The method can also include performing association analysis on the master data set to form a set of parameter/outcome association rules.

In an embodiment, the invention can include a method of programming an implantable medical device including obtaining a previously derived set of association rules. The method can also include receiving at least one parameter choice from a system user. The method can also include identifying additional parameter settings associated with the parameter choice from the system user based on the set of association rules. The method can also include suggesting the additional parameter settings to the system user.

In an embodiment, the invention can include a medical system. The medical system can include a server, the server configured to perform association analysis on a set of data representing previously programmed parameter values from a plurality of implanted medical devices to derive a set of association rules; and a device for programming an implantable medical device, the device including a user interface, the device configured to suggest parameter choices to a system user regarding a specific patient based on the derived set of association rules.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Modern IMDs of the type that include an onboard processor are generally capable of being programmed in an attempt to provide optimal therapy to a given patient. This programming generally occurs through the process of setting parameter values that influence the functioning of the device. At a basic level, parameters can include such things as pacing amplitude, pacing rate, and pulse width. At a higher level, parameters can also control device operation by allowing a system user to select between different possible algorithms for purposes such as detecting arrhythmias, responding to arrhythmias, and the like.

However, parameters frequently do not operate in isolation in terms of their effects on a patient. Rather, it is typical that several programming parameters interact together in order to deliver efficacious therapy.

Embodiments herein include systems and methods for utilizing association analysis in order to assist in the process of setting parameters for implantable medical devices.

Environment

Figure 1:
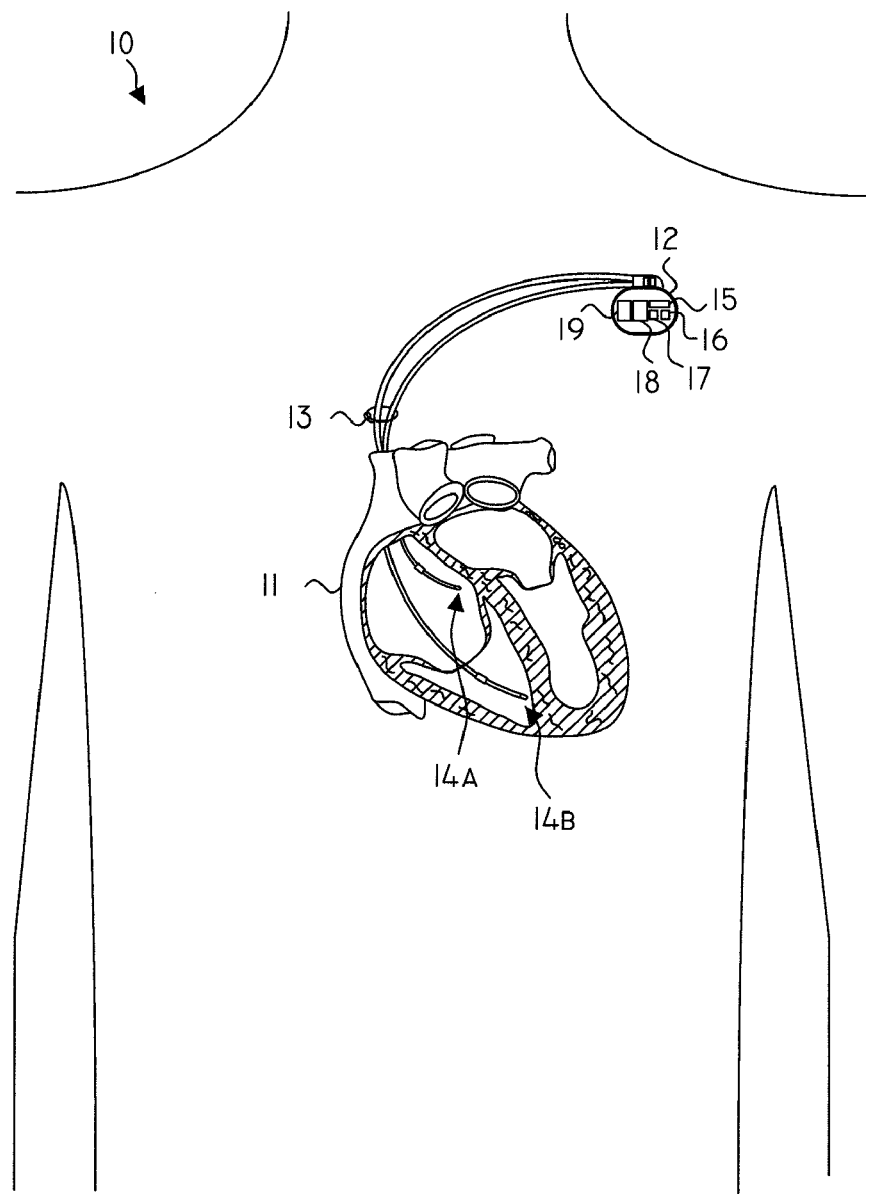
FIG. 1 is a schematic diagram showing, by way of example, an in situ cardiac rhythm management (CRM) device.

Depending upon type, CRM devices generally provide therapeutic electrical stimuli into up to three chambers of the heart. Single-chamber CRM devices typically rely on one pacing lead attached to either the right atrium or right ventricle, while dual-chamber CRM devices utilize a pair of pacing leads attached to the right atrium and right ventricle. Triple-chamber CRM devices generally use pacing leads in the right atrium, right ventricle, and coronary venous system. FIG. 1 is a schematic diagram showing, by way of example, an in situ CRM device 12 with dual-chamber pacing leads 13. CRM devices can include pacemakers, implantable cardioverter-defibrillators, and cardiac resynchronization therapy (CRT) devices, amongst others.

The CRM device 12 is surgically implanted in the chest, abdomen, or other bodily location of a patient 10 and includes a pair of pacing leads 13 for providing monitoring within and for delivering therapy to the patient's heart 11. Electrical stimuli are delivered through electrodes 14a, 14b on the distal end of each pacing lead 13. The CRM device 12 also encloses operational circuitry within a hermetically-sealed housing, which can include a transducer 15; oscillator 16; control circuitry 17; memory 18; and power source 19, which provides a finite power supply for the operational circuitry. The transducer 15 provides signal conversion, such as signals from an external device for interfacing with the CRM device 12. The oscillator 16 regulates internal device operation by controlling the timing of IMD operations. The control circuitry 17 implements the device's functionality, such as therapy delivery or physiometric monitoring. The CRM device 12 can identify arrhythmia within the patient it is implanted in. As just one example, the CRM device 12 can identify episodes of atrial tachyarrhythmia by monitoring P to P intervals electrocardiogram data as sensed through electrodes, such as electrodes on the pacing leads 13. Many other techniques of sensing tachyarrhythmia episodes can also be used by the device. Finally, the memory 18 stores recorded data, such as the patient's monitored physiometry and parametric information, including programming, status, and device operational characteristics.

Figure 2:
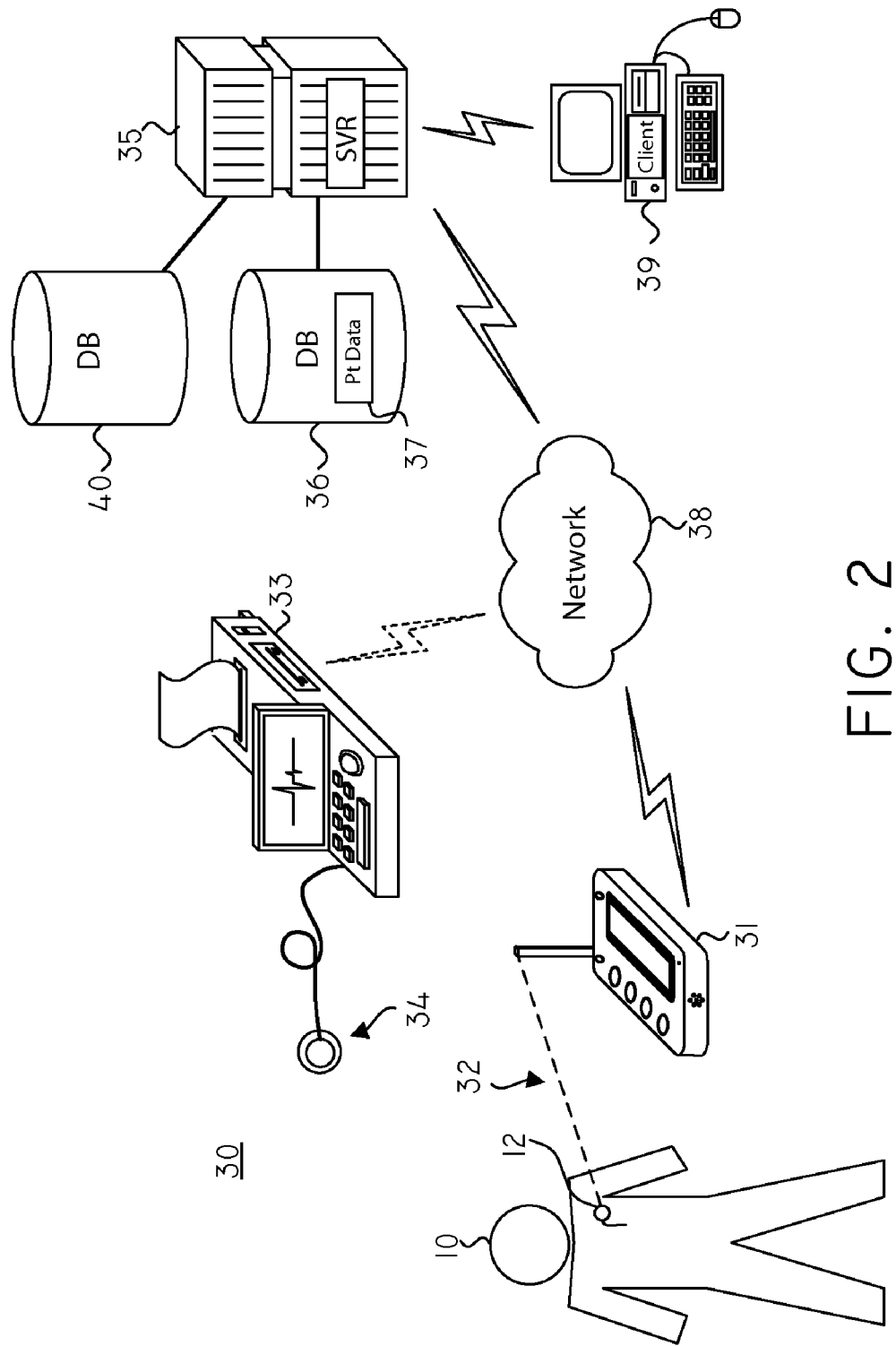
FIG. 2 is a schematic diagram showing, by way of example, an environment for interrogation of a CRM device.

Periodically, the CRM device 12 is interrogated by an external device to retrieve recorded data and download programming. FIG. 2 is a schematic diagram showing, by way of example, an environment 30 for interrogation of a CRM device 12. In addition to the CRM device 12, the environment 30 can include a repeater 31 or other patient-operable IMD interrogation device. The repeater 31 can include a processor and a memory module. The repeater 31 can include a user interface including a display screen and a user input device, such as buttons or a touch screen. The repeater 31 regularly interrogates the CRM device 12 through wireless or inductive telemetry 32 or other interfacing, either automatically, per a schedule, or on demand under patient or attendant control. Interrogations can be performed on a monthly, weekly, or daily basis, or as frequently as appropriate or practical. The repeater 31 can either store downloaded data locally, or can connect to the network 38 to store the downloaded data in the database 36.

Additionally, the environment 30 generally includes a centralized server 35 coupled to a database 36 within which patient data 37 is stored. The server 35 can include a processor and a memory module. The memory module can include RAM, ROM, or other types of memory well known to those of skill in the art. The patient data 37 can specifically include data regarding parameter settings of implantable medical devices for a plurality of patients, time stamp data, patient characteristic data (such as age, gender, diagnosed condition, etc.), outcome data (examples of which are described in greater detail below), electrogram data, and the like. In some embodiments, a database 40 for electronic medical records can also be included. The server 35 can include a processor, amongst other components. The server 35 can process the stored patient data 37 according to various methods described herein. The repeater 31 remotely interfaces with the server 35 to exchange the recorded data and programming through a network 38, such as a publicly available wide area network, including the Internet. Other forms of remote server interfacing are possible, such as described in related commonly-owned U.S. Pat. No. 7,009,511, to Mazar, issued Mar. 7, 2006, the disclosure of which is incorporated by reference.

In addition, caregivers, particularly cardiologists and electrophysiologists, are able to access the patient data 37 through a client 39 or other system interfaced to the server 35. The caregivers can also separately interrogate the CRM device 12 directly using a conventional programmer 33 that utilizes inductive or wireless telemetry 34 or other interfacing. The programmer 33 can include a processor and a memory module. The programmer 33 can include a user interface including a display screen and a user input device, such as a keyboard and/or a point device. The programmer 33 can either store downloaded data locally, or can connect to the network 38 to store the downloaded data in the database 36. Both the repeater 31 and the programmer 33 can each be considered to be a device for programming an implantable medical device.

Figure 3:
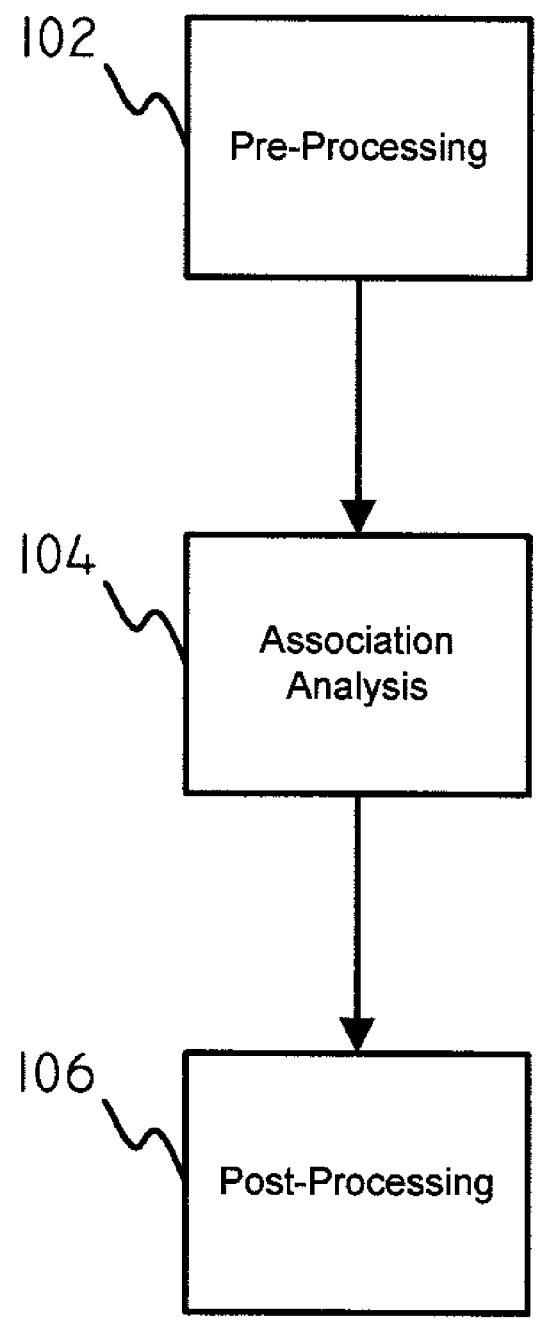
FIG. 3 is a schematic diagram of operations performed in accordance with some embodiments herein.

Referring now to FIG. 3, it will be appreciated that embodiments can include operations of pre-processing 102, association analysis 104, and post-processing 106. Various aspects of these operations will now be described in greater detail.

Association Analysis Pre-Processing

In an embodiment, derivation of association rules in the context of programming implantable medical devices is preceded by gathering a body of parameter data from previously programmed devices. In some embodiments, this body of data can be obtained in mass. In other embodiments, this body of data can be accumulated over time based on information passed to a server from a programmer (such as 33 in FIG. 2) or a repeater (such as 31 in FIG. 2). In some embodiments, the body of data can be static. In other embodiments, the body of data can be dynamic, being updated on a periodic basis or even each time new data is obtained from a device for programming an implantable medical device.

It will be appreciated that in addition to parameter data, the body of data used to derive association rules can also include other types of information. By way of example, in some embodiments the body of data used to derive association rules can also include patient outcome data. Outcome data can include, but is not limited to data regarding percentage of time spent in cardiac pacing ("percent cardiac pacing time", percentage of time spent in biventricular pacing ("percent BiV pacing time"), percentage of time spent in right ventricular pacing ("percent RV pacing time"), atrial fibrillation burden ("AF burden"), heart rate variability, patient symptom data, therapy response data, left ventricle efficiency data ("LV efficiency"), hypertension data, HF decompensation events per year ("decompensation events"), number of shocks administered, number of arrythmia episodes, survival rate, lead impedance data, amplitude of intrinsic cardiac activity ("intrinsic amplitudes"), and the like. In some embodiments, the body of data can also include characteristics about a patient, such as age, gender, NYHA (New York Heart Association) classification, weight, comorbidities, and the like. The patient outcome/characteristics or their changes over time due to programming change or disease progression can be used to derive association rules.

One or more pre-processing steps can be performed before performing association analysis on the body of parameter data. In some embodiments, pre-processing can include grouping (or segmenting) the parameter data into "records" prior to association analysis.

It will be appreciated that there are various ways of grouping the parameter data into records prior to derivation of association rules. In one embodiment, the parameter data can be grouped or segmented according to a tiered approach based on clinical relevance. At a high level, it will be appreciated that parameter data regarding anti-tachycardia therapy details, such as which ATP scheme is being used, generally only becomes relevant once anti-tachycardia therapy is itself turned on by a system user. Stated differently, if anti-tachycardia therapy is not even enabled by a system user, then details regarding anti-tachycardia therapy, such as which ATP scheme is being used, are not relevant for that particular device at that particular time. Knowledge of these logical relationships can be used in order to group parameter data into records prior to derivation of association rules.

Figure 4:
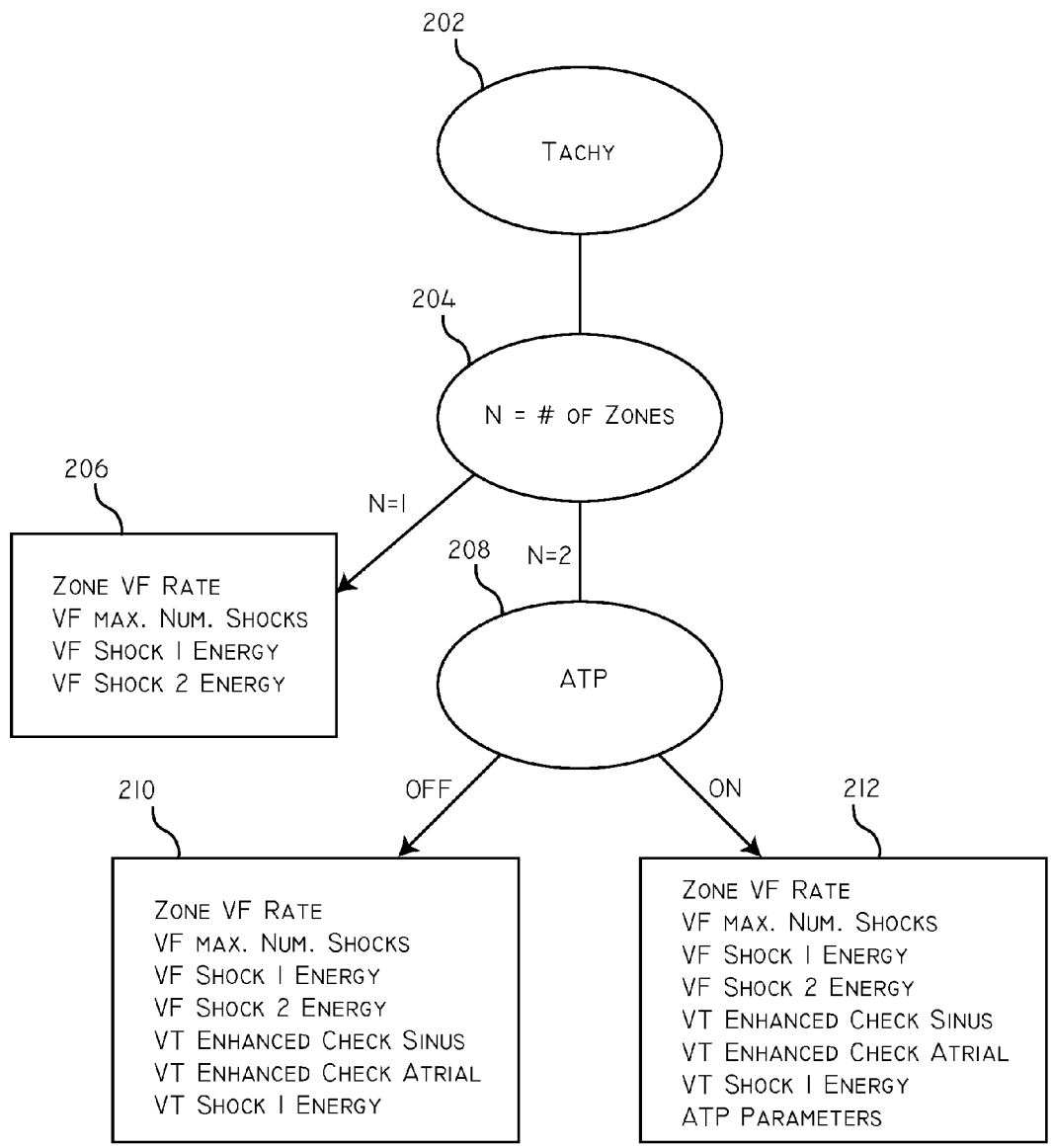
FIG. 4 is a schematic diagram illustrating logical tiers as one technique for grouping parameter data.

Referring to FIG. 4, an exemplary set of logical tiers impacting relevant parameters is shown. At the top level 202 of this logical tier is the designation "Tachy" for tachycardia that corresponds to programming parameters designed to detect and treat tachycardia. The first logical branch 204 occurs based on the number of zones recognized within tachycardia, such as to delineate between ventricular fibrillation and ventricular tachycardia, which is a programmable parameter. If there is only one zone, then a first set of parameters 206 is relevant. However, if there are two zones, then other sets of parameters are possibly relevant. For example if, anti-tachycardia pacing therapy is turned "off", then a second set of parameters 210 is relevant. However, if anti-tachycardia pacing therapy is turned "on", then a third set of parameter 212 is relevant. It will be appreciated that the specifics illustrated in FIG. 4 are but one example of how logical tiers can be used in order to derive possible sets of relevant parameters. Sets of relevant parameters can be grouped together as a record for purpose of later association analysis.

In another embodiment, the parameter data related to particular device functionalities can be grouped. In some examples, the parameters related to specific functionalities appear together on a single tab within a tabbed view from a programming interface. The value for one parameter within a single tab from a programming interface screen may have a stronger relationship to other parameter values that appear on the same tab. As such, in some embodiments, parameter data can be grouped on the basis of their functionality.

Figure 5:
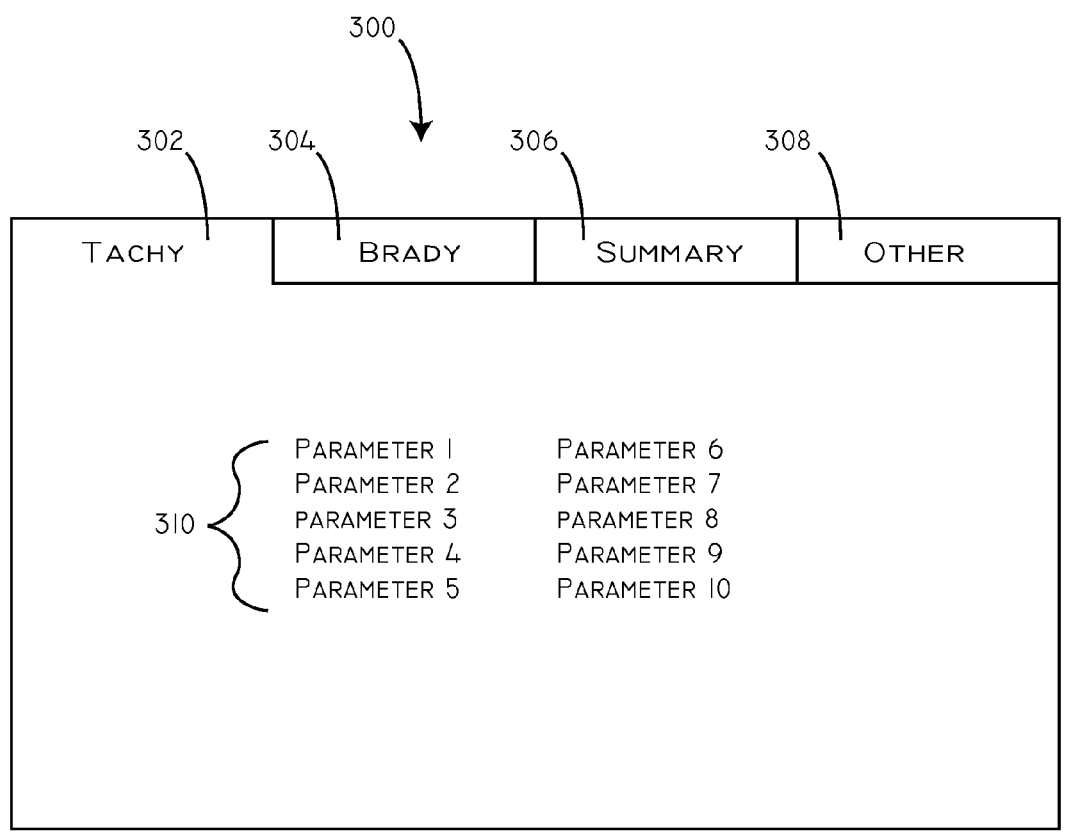
FIG. 5 is a schematic diagram illustrating grouping parameter data based on device functionality.

Referring now to FIG. 5, a schematic tabbed interface screen 300 is shown. The tabbed interface screen 300 includes a first tab 302 directed to parameters relevant to tachycardia therapy. The tabbed interface screen 300 includes a second tab 304 directed to parameters relevant to bradycardia therapy. The tabbed interface screen 300 includes a third tab 306 labeled summary including additional parameters. The tabbed interface screen 300 also includes a fourth tab 308 that may be directed to other parameters. Underneath the first tab 302 is a first set of parameters 310 with associated values. The first set of parameters 310 in this embodiment can have a logical relationship to one another in that they are all tachycardia related parameters. As such, in some embodiments, the first set of parameters 310 can be grouped together as a "record" for purposes of later association analysis processing.

In some embodiments, parameter data can be grouped according to temporal relationships between changes made to the individual parameters. For example, in one embodiment, the parameter data can be grouped according to those parameters that have had their values changed by a system user within a given programming session. By way of example, when patients visit a clinician and their device is interrogated with a programmer device, the system user may change one or more parameter values during that particular interrogation session. Within the body of parameter data then, those changes that were made during the same interrogation sessions can be grouped together as a "record" before derivation of association rules.

In another embodiment, the parameter data can be grouped by those parameter changes made over nominal values for particular devices, regardless of whether the changes are made during the same interrogation session or not. Thus, in this manner of grouping the data, the focus is more broadly directed to include the full range of changes made to the programming of a particular device, instead of just those changes made simultaneously during a given programming session. Thus, in such an embodiment, all changes made over nominal values to parameter can be grouped as a "record" for purposes of later derivation of association rules.

In another embodiment, the parameter data can be grouped according to patient characteristics. By way of example, characteristics about a patient, such as age, gender, NYHA (New York Heart Association) classification, and the like can be taken into account when grouping parameter data into logical records. For example, if patient falls within a predefined age range, then a certain set of parameter values for that patient can be taken together as a record for purposes of later association analysis. In some embodiments, the patient characteristics can be multiplex in that if the patient falls with a predefined age group and is a specific gender then a first set of parameters are grouped together, but if the patient falls with a different age group or is a different gender then a different set of parameters are grouped together.

In another embodiment, the parameter data can be grouped according to parameter settings during episodes of particular activity. By way of example, episodes of tachycardia are frequently tracked by CRM devices. In some embodiments, the parameter settings that were in place during a given episode of tachycardia can be grouped together as a record for purposes of later association analysis. The parameter data could be enhanced by including data related to the episode along with the record such as, for example, number of ATP bursts actually delivered, and outcome data such as the ATP and/or shock efficacy.

Association Analysis Algorithms

An example of a hypothetical association rule is the statement that 90% of programming sessions that change parameter values for A and B, also change parameter values for C. The "antecedent" of this rule consists of A and B and the "consequent" consists of C alone. The number 90% is the confidence factor of the rule. In many embodiments, antecedents of rules derived in accordance with embodiments herein include specific parameters and/or specific parameter values.

In some embodiments, antecedents of rules derived in accordance with embodiments herein can include patient characteristic information, outcome data, and the like.

Given a set of records (each record representing a group of parameter data), the goal of association rule mining is to find all rules having support greater than or equal to a minimum support threshold and a confidence greater than or equal to a minimum confidence threshold. Table 1 below illustrates some hypothetical records that could be subjected to association rule mining.

TABLE 1

| Record # | Data Comprising Record |
|---|---|
| 1 | Parameters A, B, E, G |
| 2 | Parameters A, C, G |
| 3 | Parameters A, B, E, F |
| N | ... |

As described above, data groups forming records can also include patient characteristic data and/or outcome data in some embodiments. Table 2 below illustrates some hypothetical records including outcome data and patient characteristics that could be subjected to association rule mining.

TABLE 2

| Record # | Data Comprising Record |
|---|---|
| 1 | Parameters A, B, E, G; Outcome #1; Patient Characteristic #1 |
| 2 | Parameters A, C, G; Outcome #2; Patient Characteristic #2 |
| 3 | Parameters A, B, E, F; Outcome #1; Patient Characteristic #4 |
| N | ... |

One technique for finding association rules, known as the brute force approach, is to list all possible association rules and then compute the support and confidence for each possible rule. Many different algorithms for deriving association rules are well known to those of skill in the art. Various techniques can be used in order to reduce the computational resources required by the brute force technique. By way of example, techniques such as frequent item set generation, the apriori principle, and the frequent pattern (FP) growth algorithm, amongst other can be used to reduce the computational burden required to derive all rules with sufficient support and confidence from the set of transactions.

In some embodiments, computation burden can be reduced by running a desired association analysis algorithm on independent data sets and then later combining rules based on the results of individual data sets.

It will be appreciated that various software tools are commercially available that can be used to derive association rules from datasets. While not limiting the scope herein, exemplary software tools can include Intelligent Miner™ (commercially available from IBM), SAS Enterprise Miner, Advanced Miner, BayesiaLab, GhostMiner, and Weka, amongst others.

Generation of association analysis rules can be performed on a periodic basis. By way of example, in some embodiments generation of new rules through association analysis can be performed every month, every week, every day, or even multiple times during a day, depending on various factors such as the size of the body of data to be processed, the computational resources available, and the like. In some embodiments, the generation of association analysis rules is a process that is handled by a separate server system or a server farm and the results, in the form of rules, can be imported back into system where they can be utilized.

Association Analysis Post-Processing

After generation of association rules, various post-processing operations can be undertaken. It will be appreciated that the raw results of association analysis can include literally thousands or tens of thousands of association rules, depending on the number of records in the total data set processed and the values used for minimum support threshold and minimum confidence threshold. Post-processing operations can be performed in order to effectuate utilization of the rules to aid in the programming process of devices.

Figure 6:
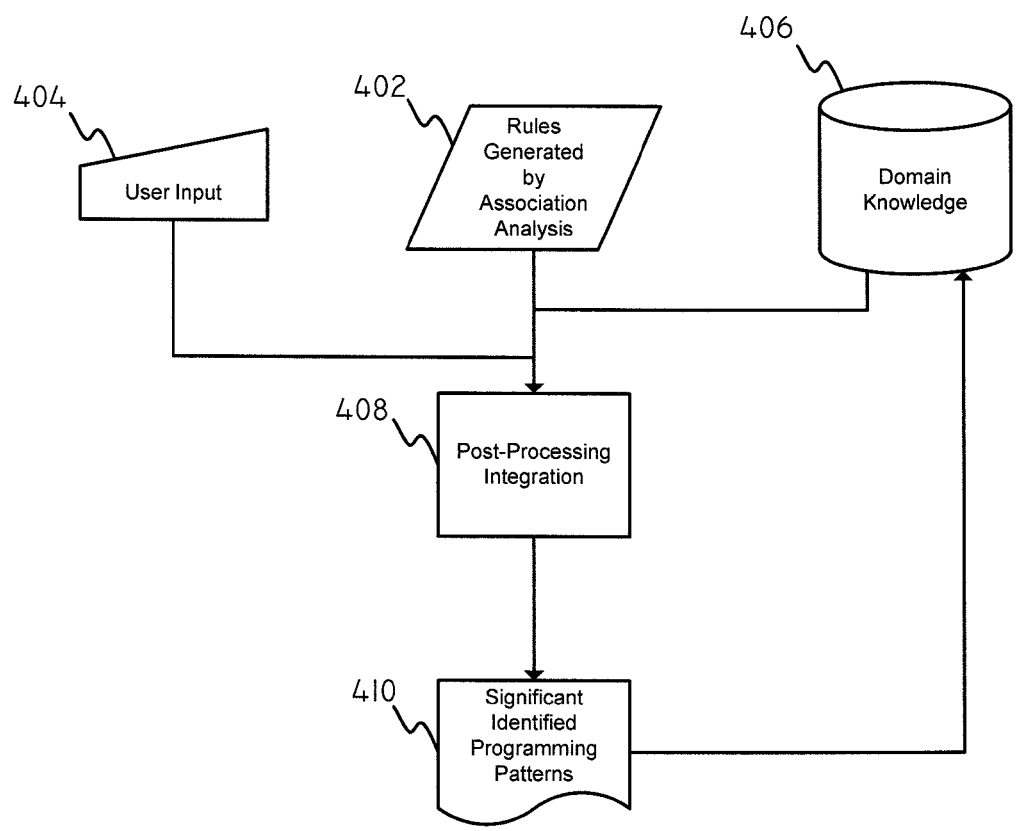
FIG. 6 is a schematic diagram illustrating various operations associated with post-processing.

Referring now to FIG. 6, a schematic diagram is shown illustrating some exemplary aspects of post-processing. A set of rules 402 can be generated according to processes and methods described above. User input 404 can be obtained. Frequently, user input 404 is obtained after the set of rules 402 is generated. However, in some embodiments, user input 404 can be obtained before the set of rules 402 is generated. It will be appreciated that in many embodiments user input may be optional.

The user input 404 can be directed to parameters of interest to the system user. For example, the system user can provide input indicating that they are interested in, for example, parameters related to tachycardia zone settings, ATP schemes, bradycardia therapy rate response settings, etc. In some embodiments, the system can infer user interest based on input in the form of changes to specific parameter settings. For example, if a system user makes a change to a tachycardia zone setting, then the system can infer that the user is generally interested in tachycardia related parameters. Once interest of the user is determined (either explicitly or inferred) then, in some embodiments, association rules related to areas of interest can be increased in weight and those relating to areas outside the scope of user interest can be decreased in weight. In some embodiments, user input can include user input directly regarding the set of rules 402 generated by association analysis. By way of example, a set of rules representing those with the highest support threshold and the highest confidence threshold can be presented to a system user and through the user input 404 the user can identify those of greatest interest, or those of most significance. This information can be used to assign weighting to the association rules.

A store of domain knowledge 406 can be also be utilized in various post-processing operations. Domain knowledge 406 can include information such as the safety of various parameter combinations, the efficacy of various parameter combinations as applied to specific disease states, association rules identified in past processing cycles, and the like.

A post-processing integration operation 408 can take as input the set of rules 402 generated from association analysis, user input 404 (if available), and a store of domain knowledge 406, and generate a set of significant identified programming patterns 410. The assignment of weight to various derived rules and/or specific parameter can be performed during post-processing operation 408. Weights can be assigned in many different ways. By way of example, weights can be assigned to individual programming parameters on the basis of clinical significance. As a hypothetical example, VT ATP time out (a parameter) could be assigned a weight of 2 and Zone VT Rate (another parameter) could be assigned a weight of 8. In some embodiments, weights can be assigned to the association between two programming parameters. As a hypothetical example, the association of Zone VF Rate (a parameter) with Zone VT Rate (another parameter) could be assigned a weight of 8. In still other embodiments, the weight of a derived rule could be assigned to be the sum of the weights of the parameters in the rule. In still other embodiments, logistic regression, or other prediction algorithms, could be used in order to predict weights on the basis of domain knowledge from a knowledge base.

In some embodiments, the presence of rules in a domain knowledge base can be the basis for assuming those rules to be significant as a given. This assumption can then be used in order to weight the derived association rules. Specifically, those rules that bear a degree of similarity to rules in the domain knowledge base can be weighted more heavily because it can be assumed that they are more likely to be significant. It will be appreciated that similarity can be gauged in many different ways. In some embodiments, similarity may be gauged by the number of overlapping antecedents between a rule in the knowledge base and a derived rule. Regardless of the specific technique used, a similarity metric score can be assigned for each derived association rule. As such, in some embodiments a method can include comparing derived rules against rules in the domain knowledge base, assigning a similarity metric to each derived rule, and weighting most heavily those derived rules with the greatest similarity metric scores.

In some embodiments, in the post-processing integration operation 408, information from the store of domain knowledge 406 can be used to knock-out rules generated by association analysis, decrease the weighting of such rules, or even increase the weighting of such rules. For example, the store of domain knowledge 406 may include data regarding which parameter setting combinations are generally regarded as inadvisable by the medical community. If one of these parameter settings combinations is part of a given derived association rule, then that rule may be discarded or otherwise marginalized so that it is not acted upon by the system. Conversely, the store of domain knowledge 406 may also include data on which parameter setting combinations are viewed as being beneficial by the medical community. If one of these beneficial parameter settings combinations is part of a given derived association rule, then that rule may be passed through to become part of the set of significant identified programming patterns 410, or at least such rules may be weighted more heavily in the course of other processing which may involve them.

In some embodiments, information from the store of domain knowledge 406 is used to identify potentially significant identified programming patterns on the basis of those rules that are not already captured by the store of domain knowledge 406 and which occur in the dataset at a frequency above a threshold value.

In some embodiments, the set of significant identified programming patterns 410 is the set of association rules with the greatest calculated weights. In some embodiments, the set of significant identified programming patterns 410 can be the set of association rules with the greatest calculated weights in addition to those rules identified through user input. Many different schemes can be used in order to select the set of significant identified programming patterns 410 from the large set of derived association rules 402.

In some embodiments, the resulting significant identified programming patterns 410 can be used to automatically update the store of domain knowledge 406. In other embodiments, the significant identified programming patterns 410 can be reviewed by a domain expert first for safety, relevance, etc., first before being fed into the store of domain knowledge 406.

In some embodiments, the set of significant identified programming patterns 410 can be used in order to make suggestions to a system user regarding potential parameter changes they may wish to consider when they are programming a given patient's CRM device. The suggestions can be positive suggestions in the sense that the suggestions can include parameter setting changes that the system user may wish to make. In some embodiments, the suggestions can also be negative suggestions in the sense that the suggestion can include parameter setting changes that the system user may wish to avoid making.

Suggestions regarding parameter setting changes made during the course of a programming session can take on various forms. In some embodiments, the system can wait to receive input from the user first regarding a first parameter change and then make suggestions to the system user regarding additional parameter changes they may wish to make. In some embodiments, the suggestions can be formulated according to outcome data. For example, if having parameters settings "A" and "B" is associated with positive outcomes (according to derived significant identified programming patterns), then upon receiving input from a user regarding selecting parameter setting "A", the system may present the user with information regarding parameter setting "B" and/or offer the choice to the system user to make that parameter setting change.

In other embodiments, the system can provide suggestions to the system user as soon as such suggestions are generated without waiting for user input. For example, in the course of a programming session, a programmer or a repeater may interrogate a device and obtain information such as the atrial fibrillation burden the patient has experienced since the last programming session. Based on this information, the system may suggest parameter changes based on rules that include combinations of parameter settings that are associated with a reduction in atrial fibrillation burden. Suggestions to system users may be provided in various forms such as through a pop-up text box, an electronic message, screen highlighting, or the like.

In some embodiments, the suggestions made to the system user may be made simply on the basis of rules describing which parameter values are frequently changed together. By way of example, if the user makes changes to parameters "c" and "d", and an association rule has been derived that changes in "c" and "d" are also associated with changes in parameter "f", then the system can make such as suggestion to the system user. In some embodiments, the suggestions can be formulated on the basis of association rules describing association between specific values of associated features. It will be appreciated that there are many grounds on which suggestions could be offered.

Exemplary Methods

Figure 7:
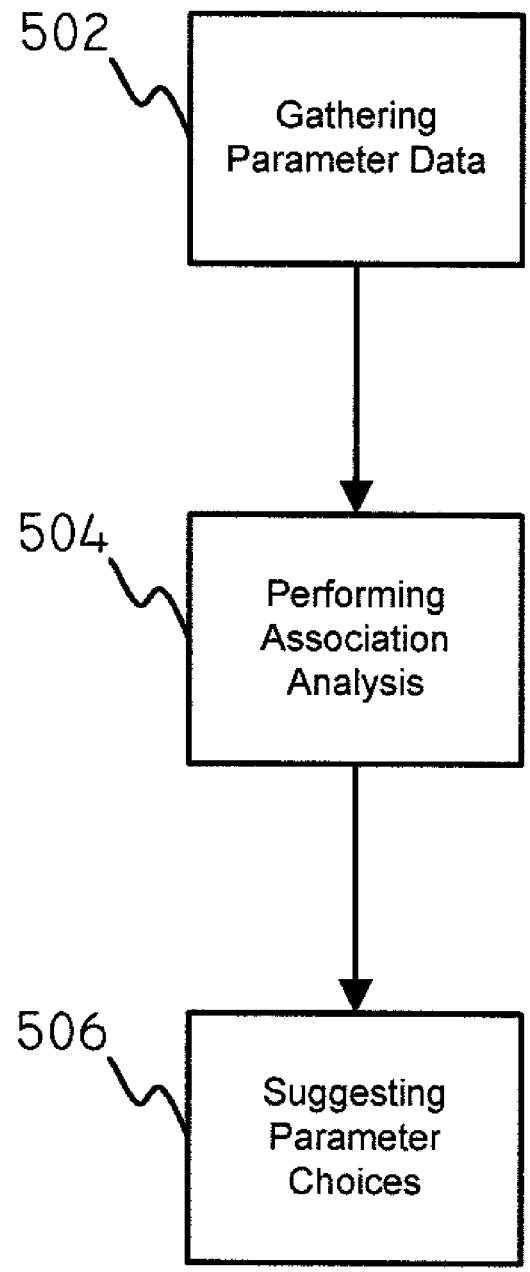
FIG. 7 is a flowchart of a method in accordance with an embodiment herein.

Based on the foregoing it will be appreciated that many different methods and processing fall within the scope described herein. One exemplary method is illustrated with respect to FIG. 7. This embodiment can be a method for programming an implantable medical device. The method can include an operation of gathering parameter data 502. The parameter data can represent a set of previously programmed parameter values from a plurality of implanted medical devices. In some embodiments, the parameter data can also accompanied by patient characteristic data and/or outcome data. The method can also include an operation of performing association analysis 504 on the parameter data to form a set of association rules. The method can also include an operation of suggesting parameter choice(s) 506 to a system user regarding a specific patient based on the set of association rules. Various aspects of these operations have been described in greater detail herein.

Figure 8:
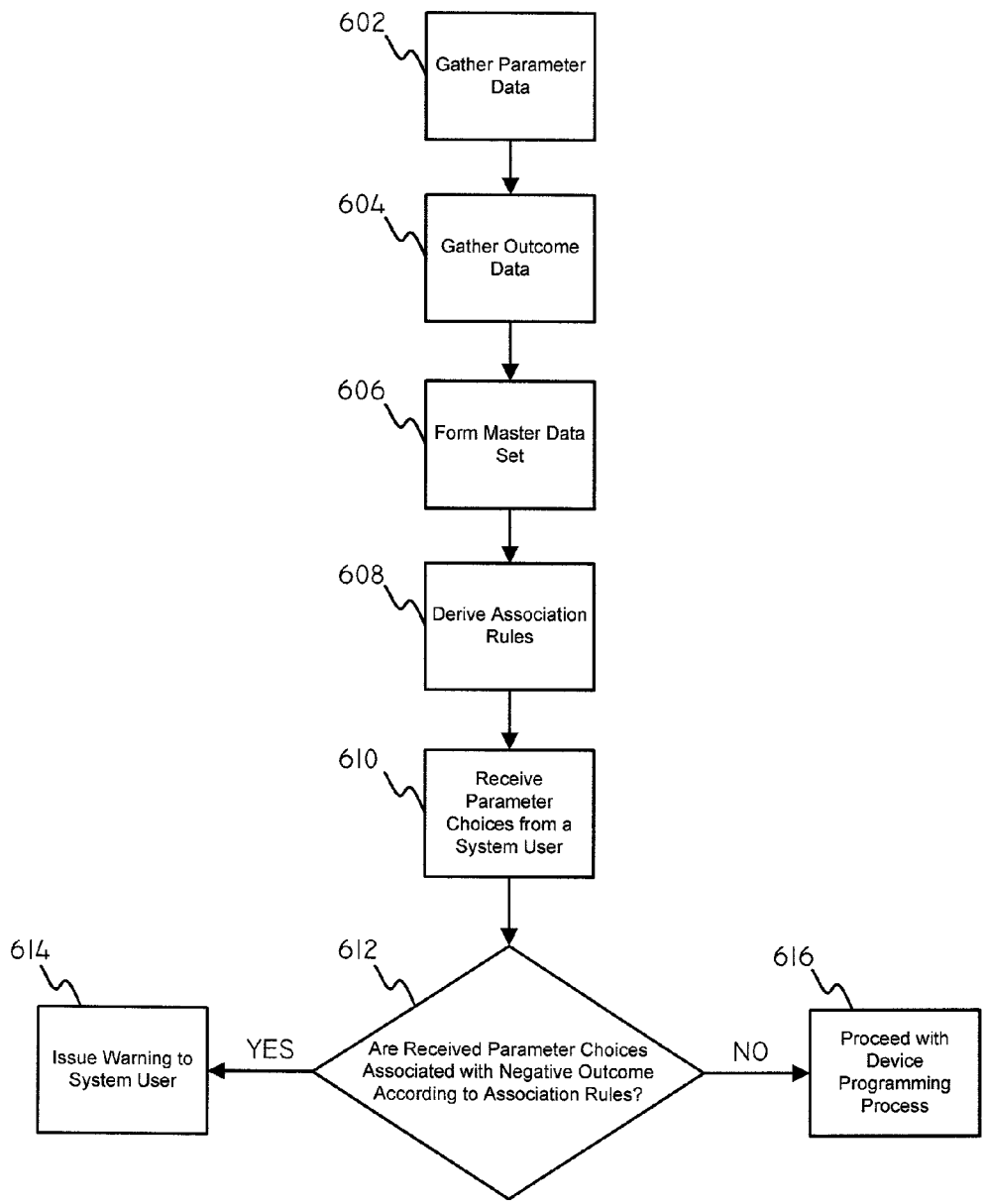
FIG. 8 is a flow chart of a method in accordance with an embodiment herein.

Another exemplary method is illustrated with respect to FIG. 8. This embodiment can also be a method for programming an implantable device. In this embodiment, an operation of gathering parameter data 602 can be included. The method can also include an operation of gathering outcome data 604 representing the effects achieved by the previously programmed parameter values. This data can be obtained from various sources including, but not limited to, user input, electronic medical records, and/or an implantable medical device. The method can also include an operation of linking the parameter data with the corresponding outcome data in order to form a master data set 606. The method can also include an operation of deriving association rules 608. The method can also include an operation of receiving a parameter choice(s) from a system user 610. The parameter choice can be received as input through a device for programming an implantable medical device. The device for programming an implantable medical device may either be in physical proximity with an implanted medical device to be programmed or may be at a remote location. The method can also include an operation of determining whether or not the received parameter choices are associated with negative outcomes according to the derived association rules 612. If the received parameter choices are associated with negative outcomes, then the system can issue a warning 614 to a system user. The warning may be in various forms. By way of example, the warning may be in the form of a pop-up box, a highlighted area, a grayed out value or button, or the like. However, if the received parameter choices are not associated with negative outcomes, then the system can allow the device to proceed with the programming process 616. In some embodiments, the system can query the user to allow the user to approve or disapprove the parameter choices, such as after operation 612 and before operation 616.

It will be appreciated that in some embodiments association rules may be derived well in advance of a programming session. As such, in some embodiments, previously derived sets of association rules may be obtained and then used in the course of a programming session. For example, in an embodiment, a method of programming an implantable medical device herein includes operations of obtaining a previously derived set of association rules, receiving at least one parameter choice from a system user, identifying additional parameter settings associated with the parameter choice from the system user based on the set of association rules, and suggesting the additional parameter settings to the system user.

Exemplary Parameters

It will be appreciated that the number of potential parameters to be evaluated can be quite large. The precise number and identity of parameters will, of course, depend on the specific CRM devices representing data in the data set. A limited set of exemplary parameters is shown below in Table 3. However, it will be appreciated that this set is provided by way of illustration only and that the scope of parameters which is included herein shall not be limited by this set.

TABLE 3

| Initial VF Duration | Zone VT1 Rate |
| --- | --- |
| Zone VF Rate | VT ATP1 Ramp Decrement |
| VT ATP1 Initial Pulses | VT ATP2 Ramp Decrement |
| VT ATP2 Initial Pulses | VT ATP1 Number of Bursts |
| VT ATP1 Scan Decrement | VT ATP2 Number of Bursts |
| VT ATP2 Scan Decrement | VT1 ATP1 Number of Bursts |
| VT ATP1 Burst Cycle Length | VT1 ATP2 Number of Bursts |
| VT ATP2 Burst Cycle Length | VT1 ATP1 Initial Pulses |
| VT Onset Value | VT1 ATP2 Initial Pulses |

TABLE 3-continued

| Initial VF Duration | Zone VT1 Rate |
| --- | --- |
| Zone VT Rate | VT1 ATP1 Scan Decrement |
| Initial VT Stability Threshold | VT1 ATP2 Scan Decrement |
| Initial VT1 Stability Threshold | VT1 ATP1 Ramp Decrement |
| VT1 Onset Value | VT1 ATP2 Ramp Decrement |
| Initial VT1 Duration | VT1 ATP1 Burst Cycle Length |
| | VT1 ATP2 Burst Cycle Length |

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

The invention claimed is:

1. A method of programming an implantable medical device comprising:
    gathering parameter data representing a set of previously programmed parameter values from a plurality of implanted medical devices;
    performing association analysis on the parameter data to form a set of association rules; and
    suggesting parameter choices to a system user regarding a specific patient based on the set of association rules.

2. The method of claim 1, further comprising receiving at least one parameter choice from a system user, wherein suggesting parameter choices to a system user is based on an association rule that includes the at least one parameter choice from the system user as an antecedent.

3. The method of claim 1, further comprising obtaining information regarding the specific patient, wherein suggesting parameter choices to a system user is based on the association rules and the information regarding the specific patient.

4. The method of claim 3, wherein suggesting parameter choices to a system user is based on an association rule that includes the information regarding the specific patient as an antecedent.

5. The method of claim 1, wherein the information regarding the specific patient is obtained from at least one of the implantable medical device, a system user, or an electronic medical record.

6. The method of claim 1, further comprising grouping together parameter data reflecting changes made within the same programming session for particular patients.

7. The method of claim 1, further comprising grouping together parameter data reflecting changes made over nominal parameter values for particular devices.

8. The method of claim 1, further comprising grouping together parameter data based on parameters related to a particular device functionality.

9. The method of claim 1, further comprising subdividing the parameter data into patient characteristic groups based on at least one of patient characteristic and patient outcome data.

10. The method of claim 1, further comprising
subdividing the parameter data into patient groups based on at least one of patient characteristic and patient outcome data;
selecting an appropriate subdivided patient group associated with a positive outcome based on at least one characteristic of the patient being treated by the system user; and
suggesting parameter choices based on the association rules for the patient being treated by the system user.

11. The method of claim 1, further comprising performing one or more post-processing operations after performing association analysis and before suggesting parameter choices.

12. The method of claim 11, wherein post-processing operations include cross-referencing association rules derived during association analysis against a domain knowledge base.

13. The method of claim 11, wherein post-processing operations include updating a domain knowledge base using association rules derived during association analysis.

14. The method of claim 11, wherein post-processing operations include selecting a subset of association rules derived during association analysis based upon at least one of user input and data from a domain knowledge base.

15. A method of programming an implantable medical device comprising:
gathering parameter data representing a set of previously programmed parameter values from a plurality of implantable medical devices;
gathering outcome data representing the effects achieved by the previously programmed parameter values from the plurality of implanted medical devices;
linking the parameter data with the corresponding outcome data to form a master data set;
performing association analysis on the master data set to form a set of parameter/outcome association rules; and
suggesting parameter choices to a system user regarding a specific patient based on the set of association rules.

16. The method of claim 15, further comprising
receiving parameter choices from a system user for treatment of a patient; and
issuing a warning to the system user if the received parameter choices are associated with a negative outcome according to the parameter/outcome association rules.

17. The method of claim 15, the outcome data comprising at least one of percent cardiac pacing time, percent BiV pacing time, percent RV pacing time, AF burden, heart rate variability, patient symptom data, therapy response data, LV efficiency, hypertension data, decompensation events, number of shocks administered, number of arrhythmia episodes, survival rate, lead impedance data, and intrinsic amplitudes.

18. A medical system comprising:
a server comprising a processor and a memory module, the server configured to perform association analysis on a set of data representing previously programmed parameter values from a plurality of implanted medical devices to derive a set of association rules; and
a device for programming an implantable medical device, the device including a user interface, the device configured to suggest parameter choices to a system user regarding a specific patient based on the derived set of association rules.

19. The medical system of claim 18, wherein the device for programming is configured to receive at least one parameter choice from a system user through the user interface, wherein suggested parameter choices to the system user are based on an association rule that includes the at least one parameter choice from the system user as an antecedent.

20. The medical system of claim 18, the system further configured to perform one or more post-processing operations after the server performs association analysis and before the device for programming an implantable medical device suggests parameter choices; the one or more post-processing operations including cross-referencing association rules derived during association analysis against a domain knowledge base.

* * * * *